United States Patent
Guo et al.

(10) Patent No.: US 9,617,575 B2
(45) Date of Patent: Apr. 11, 2017

(54) HIGH CONCENTRATION METHANOL TOLERANT METHANOTROPH AND ITS APPLICATION

(71) Applicant: Tianjin institute of industrial biotechnology, Chinese academy of science, Tianjin (CN)

(72) Inventors: Wei Guo, Tianjin (CN); Demao Li, Tianjin (CN); Shulin Chen, Tianjin (CN)

(73) Assignee: Tianjin Institute of Industrial Biotechnology, Chinese Academy of Science, Tianjing (CN)

( * ) Notice: Subject to any disclaimer, the term of this patent is extended or adjusted under 35 U.S.C. 154(b) by 0 days.

(21) Appl. No.: 14/988,761

(22) Filed: Jan. 6, 2016

(65) Prior Publication Data
US 2016/0201106 A1    Jul. 14, 2016

(51) Int. Cl.
C12P 5/00 (2006.01)
C12P 23/00 (2006.01)
C12R 1/26 (2006.01)
C12P 19/04 (2006.01)
C12N 1/20 (2006.01)

(52) U.S. Cl.
CPC .............. *C12P 23/00* (2013.01); *C12N 1/20* (2013.01); *C12P 19/04* (2013.01); *C12R 1/26* (2013.01); *Y02E 50/343* (2013.01)

(58) Field of Classification Search
CPC ...................................................... C12P 5/007
See application file for complete search history.

(56) References Cited

U.S. PATENT DOCUMENTS

2002/0137190 A1*  9/2002  Koffas ............... C12N 1/20
                                                     435/252.3

* cited by examiner

*Primary Examiner* — Rosanne Kosson
(74) *Attorney, Agent, or Firm* — Platinum Intellectual Property LLP

(57) ABSTRACT

The present invention discloses a high concentration methanol tolerant methanotroph and its application, a accession number of the methanotroph in China General Microbiological Culture Collection Center being CGMCC No. 9873, deposit date being Oct. 29, 2014, category names being *Methylomonas* sp. ZR1. The methanotroph *Methylomonas* sp. ZR1 disclosed by the present invention can grow rapidly by using methane, and can tolerate with high concentration of methanol. The methanotroph *Methylomonas* sp. ZR1 can use $C_1$ compounds such as methane and methanol to produce high value-added products such as carotenoids and polysaccharides, which has high application prospect in biological transformation of one-carbon chemistry.

4 Claims, 8 Drawing Sheets

SEQUENCE LISTING

```
<160> NUMBER OF SEQ ID NOS: 1

<210> SEQ ID NO 1
<211> LENGTH: 1353
<212> TYPE: DNA
<213> ORGANISM: Artificial Sequence
<220> FEATURE:
<223> OTHER INFORMATION: This artificial sequence obtained by amplifying
      16S rRNA sequence of methanotroph genome

<400> SEQUENCE: 1
aacgtattca ccgcggcatt ctgatccgcg attactagcg attccgactt cacgcagtcg      60
agttgcagac tgcgatccgg actgggaccg gcttttggg attcgcttac tctcgcgagt     120
tcgcagccct ctgtaccggc cattgtagca cgtgtgtagc cctacccata agggccatga     180
tgacttgacg tcgtcccac cttcctccgg tttatcaccg gcagtctccc tagagttccc     240
ggcatgaccc gctggcaact aaggataagg gttgcgctcg ttacgggact taacccaaca     300
tttcacaaca cgagctgacg acagccatgc agcacctgtc tcagagttcc cgaaggcact     360
ccgctatctc taacagattc tctggatgtc aagggtaggt aaggttcttc gcgttgcatc     420
gaattaaacc accatgctcc accgcttgtg cgggccccg tcaattcatt tgagttttag     480
ccttgcggcc gtactcccca ggcggtcaac ttaatacgtt agctccacta ctaagttctt     540
taagaaccca acagttagtt gacatcgttt acggcgtgga ctaccagggt atctaatcct     600
gtttgctacc cacgctttcg tacctcagcg tcagttttag tccagggagc cgccttcgcc     660
actggtgttc cttcagatct ctacgcattt caccgctaca cctgaaattc cactcccctc     720
tactaaactc tagttgccca gtatcaaatg cagttcccag gttaagccca gggctttcac     780
atctgactta aacaaccgcc tacgcacgct ttacgcccag taattccgat taacgcttgc     840
accctccgta ttaccgcggc tgctggcacg gagttagccg gtgcttcttg tataggtaat     900
```

```
gtcagtctac cgggtattaa ccgataggta ttccttccta ttgaaagtgc tttacaaccc    960
tcaggccttc ttcacacacg cggtattgct ggatcaggct ttcgcccatt gtccaatatt   1020
ccccactgct gcctcccgta ggagtctggg ccgtgtctca gtcccagtgt ggctgatcat   1080
cctctcagac cagctacgga tcgtcgcctt ggtaggcctt taccccacca actagctaat   1140
ccgacatagg ctcatctatt agcgccaggc ccgaaggtcc ccagctttcc cccgtagggc   1200
gtatgcggta ttagcgtgag tttccccacg ttgtccccca ctaataggca gattcctatg   1260
cattactcac ccgtccgcca ctcgtcagcg cccgaaggcc tgctaccgtt cgacttgcat   1320
gtgttaagca taccgccagc gttcaatctg agc                                1353
```

HIGH CONCENTRATION METHANOL TOLERANT METHANOTROPH AND ITS APPLICATION

The present invention incorporates by reference the material in the ASCII text file whose name is sample sequence listing, the date of creating the ASCII text file is 29 Dec. 2015, and the size of the ASCII text file is 2552 bytes.

The *methylomonas* referred to as SP.ZR1 has the China General Microbiological Culture Collection Center (CGMCC) designation number CGMCC NO. 9873, having been deposited on Oct. 29, 2014.

The address of CGMCC: No. 3, No. 1, Beichen West Road, Chaoyang District, Beijing The telephone number:0086-10-64807355

The e-mail: cgmcc@im.ac.cn

FIELD OF THE INVENTION

The present invention relates to the art of application technology about microorganisms, and particularly relates to a high concentration methanol tolerant methanotroph and its application.

DESCRIPTION OF THE RELATED ART

The world possesses a huge amount of methane, which is mainly in Siberia Marsh (about 8 ten billion tons), in the Polar Ice Sheet (about five hundred billion tons) and in the Sea Bed (about 2.5 to 10 megatons), meanwhile, there are a lot of unconventional sources of methane on earth, such as coalbed methane, landfill gas, biogas, marine methane hydrates and methane recovered from the coke oven gas and refinery gas. Methane is a greenhouse gas whose warming power of the atmosphere is 23 times stronger than carbon dioxide. Currently methane is used as fuel by human primarily. Converting methane into higher value chemicals and liquid fuels can provide significantly economic value, and environmental and strategic interests.

Currently conversion process of methane is indirect in industry, which mainly includes three steps. They are complex and multistage processes, and are operated under severe conditions such as: steam reforming at 800~1000° C., and 20~30 ATM; partly oxidizing at 1200~1500° C. and methanol synthesizing at 200~300° C. and 50~100 ATM. While microorganisms can convert methane into various metabolic intermediates with different carbon chain length at room temperature and atmospheric pressure, a biotechnology of converting microorganisms into methane has good potential and prospect.

Commercial bioconversion of methane has gone through three stages: 1) producing single cell protein, 2) using methane monooxygenase to produce ethylene oxide, and 3) biodegradating chloride contaminants. Meanwhile, only using methane monooxygenase to produce ethylene oxide has achieved a certain economic benefits until now. An important factor of limiting the industrialization of converting methane by using microorganisms is low growth rate of the microorganisms.

Methanol is the main product of methane conversion process, and is the main product of coal chemical industry. Methanol is also the basic material of $C_1$ chemical industry. Methanol has wide raw material sources, and its biggest usage is to produce other oxygen-containing organic chemicals, such as formaldehyde, acetic acid and ether. The research for biological conversion of methanol is still at the laboratory stage. Producing single cell protein by fermenting which uses methanol as substrate is the most typical application of biotechnology in the development of methanol derived product. Methanol can be directly used by methanotroph, but methanol has a relatively strong physiological toxicity to methanotroph. Methanotrophs which have been reported show poor ability to tolerate methanol. For example, *Methylomonas lenta* exhibits sensitiveness to culture medium added with 0.1% to 0.5% methanol. The methanotroph which has been mutagenized can tolerate 2.4% methanol, but shows poor stability. While the methanotroph disclosed by the present invention which is wild without being mutagenized can still grow when the concentration of methanol in culture medium reaches 3.5%.

At present, the patents about methanotroph in China mainly relate to cultural method of methanotroph, application of methanotroph in wastewater treatment, production of single cell protein and production of methanol. Parts of the patents have disclosed producing PHA by fermenting of methanotroph.

The methanotroph disclosed by the present invention can grow efficiently using methane, and can tolerate to high concentration of methanol. A good foundation is established for using the methanotroph to ferment methane or methanol to produce high value-added products such as carotenoids and polysaccharides.

SUMMARY OF THE INVENTION

One purpose of the present invention is to disclose a high concentration methanol tolerant methanotroph. The methanotroph disclosed by the present invention is screened from wetlands of sludge, and the methanotroph can grow rapidly by using methane, and the methanotroph can tolerate with high concentration of methanol.

Further, one purpose of the present invention is to provide an application of a high concentration methanol tolerant methanotroph. The methanotroph disclosed by the present invention can produce carotenoids in liquid fermentation culture medium with methanol or methane as substrate.

Further, one purpose of the present invention is to provide an application of a high concentration methanol tolerant methanotroph. The methanotroph disclosed by the present invention can produce polysaccharide in liquid fermentation culture medium with methanol or methane.

To achieve the above objects and other objects, the present invention adopts the technical scheme, the present invention provides:

A high concentration methanol tolerant methanotroph named *Methylomonas* sp. ZR1, an accession number of the methanotroph in China General Microbiological Culture Collection Center of the methanotroph is CGMCC No. 9873, and deposit date of the methanotroph is Oct. 29, 2014.

An application of the high concentration methanol tolerant methanotroph is for producing carotenoids.

Preferably, the carotenoids is produced by fermentation product which is obtained from inoculating and fermenting the methanotroph with methane or methanol as substrate in a fermentation temperature of 20~30° C.

Preferably, the fermentation temperature is 25° C.

Preferably, when the methanol is used as substrate, the mass percent concentration of the methanol in the fermentation culture medium is less than or equal to 3.5%.

An application of the high concentration methanol tolerant methanotroph is for producing polysaccharide.

Preferably, polysaccharides are produced by the fermentation product, which is obtained from inoculating and fermenting of the methanotroph with methane or methanol as substrate in a fermentation temperature of 20~30° C.

Preferably, the fermentation temperature is 25° C.

Preferably, when the methanol is used as substrate, the mass percent concentration of the methanol in the fermentation culture medium is less than or equal to 3.5%.

Preferably, the polysaccharide is heteropolysaccharide which mainly includes glucosamine, glucose and mannose.

Morphological characteristics of colonies of the methanotroph which is disclosed by the present invention are as follows:

circular smooth colonies with central uplift and smooth edges are generated on NMS culture medium, the colonies of the methanotroph show brightly orange and thick, Gram staining of the cells of the methanotroph is negative.

The beneficial effects of the present invention are as follows:

The advantages the methanotroph disclosed by the present invention are as follows:

① being easy to cultivate: the methanotroph can grow well in NMS culture medium with methane as carbon source, wherein recipe of the NMS culture medium is simple, wherein there is no need to add organic nitrogen into the NMS culture medium;

② growing rapidly with methane as carbon source: single colony of the methanotroph is picked and inoculated into the NMS culture medium with methane as substrate and with inorganic as nitrogen source; after being cultured for 48 h, the cell concentration of the methanotroph can reach $10^8$ cfu/ml;

③ tolerating with high concentration of methanol: the methanotroph can grow well in the NMS culture medium with methanol as substrate, wherein concentration of methanol is 35 g/L; after being cultured for 3 days, $OD_{600}$ of the NMS culture medium can reach 2.5;

④ producing carotenoids and polysaccharides with methane and methanol as substrates:

After being cultured for 10 days with methane as substrate, fermentation broth of the methanotroph appears to be bright orange viscous liquid because of carotenoids and polysaccharides produced by the methanotroph;

After being cultured for 3 days with methanol as substrate, fermentation broth of the methanotroph appears to be bright orange viscous liquid because of carotenoids and polysaccharides produced by the methanotroph;

As described above, a high concentration methanol tolerant methanotroph *Methylomonas* sp. ZR1 is obtained by screening in the present invention, and the methanotroph *Methylomonas* sp. ZR1 can use methane to grow rapidly, and can use $C_1$ compounds such as methane and methanol to produce high value-added products such as carotenoids and polysaccharides. The methanotroph *Methylomonas* sp. ZR1 has good potential and prospect in biological transformation of $C_1$ compounds. The methanotroph *Methylomonas* sp. ZR1 disclosed by the present invention is applied to produce polysaccharide and carotenoids, wherein the producing process is simple and the operation of the producing is easy. The methanotroph *Methylomonas* sp. ZR1 can grow rapidly by using methane or methanol, and can produce carotenoids and polysaccharides with high added value. Meanwhile the methanotroph *Methylomonas* sp. ZR1 can tolerate with high concentration of methanol and has a high industrial application value.

DETAILED DESCRIPTION OF THE INVENTION

The present invention will be further described in detail with the accompanying drawings, to make those skilled in the art can implement the invention according to the text of the specification.

If there is no special instruction, experimental methods used in the following embodiments are conventional methods.

If there is no special instructions, materials and reagents used in the following embodiments can be obtained from commercial sources.

The solvent in the NMS culture medium is water, and the solute in the NMS culture medium is $KNO_3$ 1 g/L, $KH_2PO_4$ 0.717 g/L, $Na_2HPO_4$ 0.272 g/L, $MgSO_4 \cdot 7H_2O$ 1 g/L, $CaCl_2 \cdot 6H_2O$ 0.2 g/L, sodium iron EDTA 0.005 g/L and 1 ml of trace element solution; when methane is used as carbon source or substrate, the methane accounts for 15~50% of gas and air accounts for 50~80% of gas; when methanol is used as carbon source or substrate, the adding content of the methanol is 1.0~3.5%.

Solid medium is prepared by adding 15 g of agar per liter of the NMS culture medium.

The trace element solution is prepared by adding EDTA 0.5 g, $FeSO_4 \cdot 7H_2O$ 0.2 g, $H_3BO_3$ 0.03 g, $ZnSO_4 \cdot 7H_2O$ 0.01 g, MnCl$_2$.4H$_2$O 0.003 g, CoCl$_2$.6H$_2$O 0.02 g, CuSO$_4$.5H$_2$O 0.1 g, NiCl$_2$.6H$_2$O 0.002 g and Na$_2$MoO$_4$ 0.003 g per liter of water.

Embodiment 1

Screening Method of Methanotroph *Methylomonas* sp. ZR1

The methanotroph *Methylomonas* sp. ZR1 is screened from wetland of sludge, 1 g sample of wetland of sludge is inoculated directly into 250 ml anaerobic bottle containing 100 ml of the NMS culture medium, 100 ml of methane is added to the anaerobic bottle as carbon source to make methane account for 30% of gas phase in the anaerobic bottle. The methanotroph is cultured in shake at 25° C. and at 180 rpm until that OD$_{600}$ of the NMS culture medium can hold steady. The methanotroph is inoculated into fresh culture medium with 1% inoculation, and is subcultured 3 times; the liquid culture is diluted and coated on coated tablet, and the coated tablet is placed in air with methane accounting for 30%. A large amount of the methanotroph can be obtained by using the screening method, wherein the methanotroph *Methylomonas* sp. ZR1 which generates bright orange colonies grows fastest and generates the largest colony.

Genome of the methanotroph is extracted, and 16S rRNA gene sequences of the genome are amplified and sequenced; polynucleotide sequences of 16S rRNA are the same as polynucleotide sequence of SEQ ID No:1; with the 16S rRNA gene sequences compared with the Blast results in NCBI, the comparison results show that the 16S rRNA gene sequences have a 97.9% similarity with *Methylomonas methanica* S1$^T$; according to the comparison results combined with physiological and biochemical characteristics of methanotroph *Methylomonas* sp. ZR1, the methanotroph is assigned as *Methylomonas* sp ZR1.

Embodiment 2

Methanotroph *Methylomonas* sp. ZR1 Growing with Methane as Substrate

Figure 1:
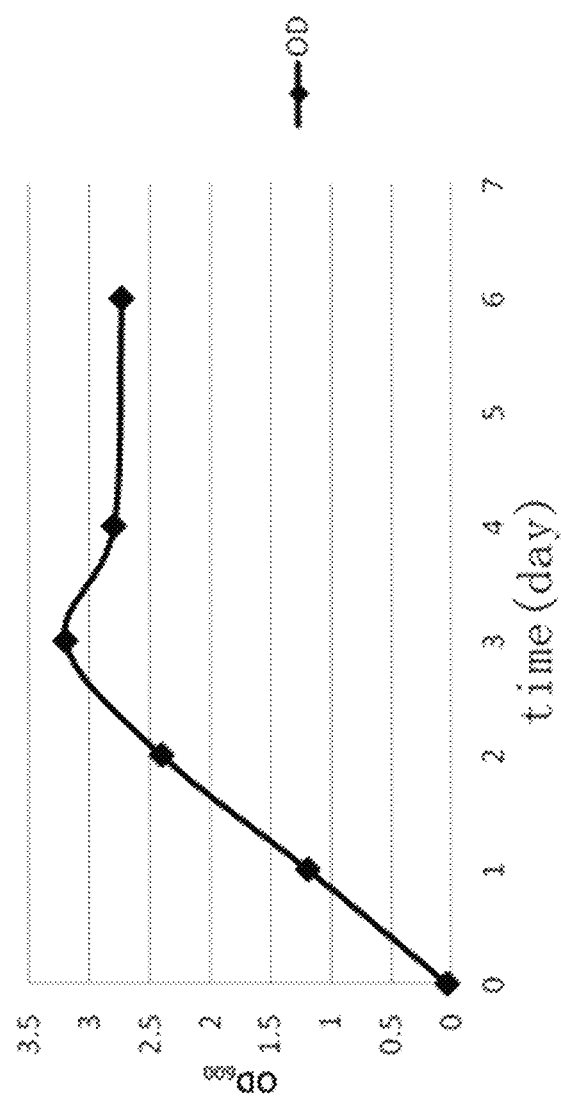
FIG. 1 is a growth curve of the high concentration methanol tolerant methanotroph *Methylomonas* sp. ZR1 disclosed by the present invention with methane as substrate.

Single colony of the methanotroph *Methylomonas* sp. ZR1 formed on the plate is picked, inoculated into 30 ml of NMS liquid culture medium (using methane as carbon source) to culture at 28° C. and at 180 rpm; samples of fermentation broth are taken and cell concentration of the samples is measured every day; as shown in the FIG. 1, the cell concentration increases with the extension of fermentation time, which shows the number of the methanotroph *Methylomonas* sp. ZR1 gradually increases and the methanotroph *Methylomonas* sp. ZR1 grow well in the NMS liquid culture medium with methane as substrate.

Embodiment 3

Methanotroph *Methylomonas* sp. ZR1 Growing with Methanol as Substrate

Figure 2:
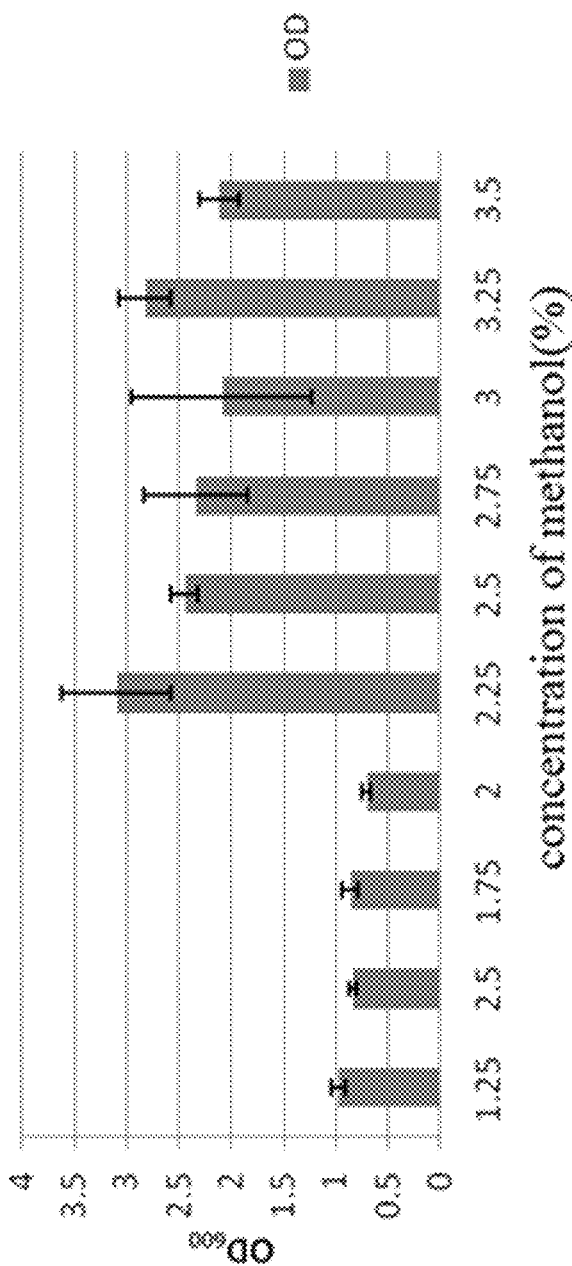
FIG. 2 is a growth comparison chart of the high concentration methanol tolerant methanotroph *Methylomonas* sp. ZR1 disclosed by the present invention with different concentration of methanol as substrate.

Single colony of the methanotroph *Methylomonas* sp. ZR1 is obtained by the methanotroph *Methylomonas* sp. ZR1 growing with methanol as substrate, the single colony of the methanotroph *Methylomonas* sp. ZR1 is inoculated into 30 ml of NMS liquid culture medium (using methane as carbon source) to culture at 28° C. and at 180 rpm. After being cultured for 2 days, OD$_{600}$ of the NMS liquid culture medium reaches 0.7, inoculated into 100 ml of fresh NMS culture medium with 5% inoculation, wherein the content of methanol in the fresh NMS culture medium is respectively 12.5 g/L, 15 g/L, 17.5 g/L, 20 g/L, 22.5 g/L, 25 g/L, 27.5 g/L, 30 g/L, 32.5 g/L and 35 g/L, and be cultured in shake for 3 days at 25° C. and at 180 rpm in a 250 ml shake flasks; cultivation results are shown in FIG. 2, which show the methanotroph *Methylomonas* sp. ZR1 can grow and reproduce well in the culture medium with different concentration of methanol.

Embodiment 4

Fermenting Methanotroph *Methylomonas* sp. ZR1 to Produce Carotenoids with Methane as Substrate Single colony of the methanotroph *Methylomonas* sp. ZR1 formed on the plate is picked, inoculated into 30 ml of NMS liquid culture medium (using methane as carbon source) to culture at 25° C. and at 180 rpm, after being cultured for 2 days, OD$_{600}$ of the NMS liquid culture medium reaches 0.7, and inoculated into fresh NMS culture medium with 5% inoculation, fermenting in column reactor at 28° C.; after being cultured for 2 days, fermentation broth of single colony of the methanotroph *Methylomonas* sp. ZR1 appears to be orange viscous liquid; the methanotroph *Methylomonas* sp. ZR1 is collected by centrifugation for 10 mins at 8000 rpm; the methanotroph *Methylomonas* sp. ZR1 collected is washed twice with distilled water, vacuum freeze-dried, then dried powder of the methanotroph is obtained; the dried powder of the methanotroph *Methylomonas* sp. ZR1 is weighed, and is extracted 3 times with methanol solution whose volume is 10 times the volume of dried powder of the methanotroph *Methylomonas* sp. ZR1, then orange extraction solution of pigment is obtained; the orange extraction solution of pigment is filtered, and spin dried by a rotary evaporation apparatus, then red pigment is obtained.

The Color Reaction of the Red Pigment in Concentrated Sulfuric Acid

The extracted red pigment is re-dissolved in 1 ml of dichloromethane, then pigment solution is obtained; 50 µl of the pigment solution was taken, diluted with chloroform to 0.5 ml, and being added with a few drops of concentrated sulfuric acid; then the pigment solution turns from red to blue-green, which shows that the red pigment extracted is carotenoids.

Figure 3:
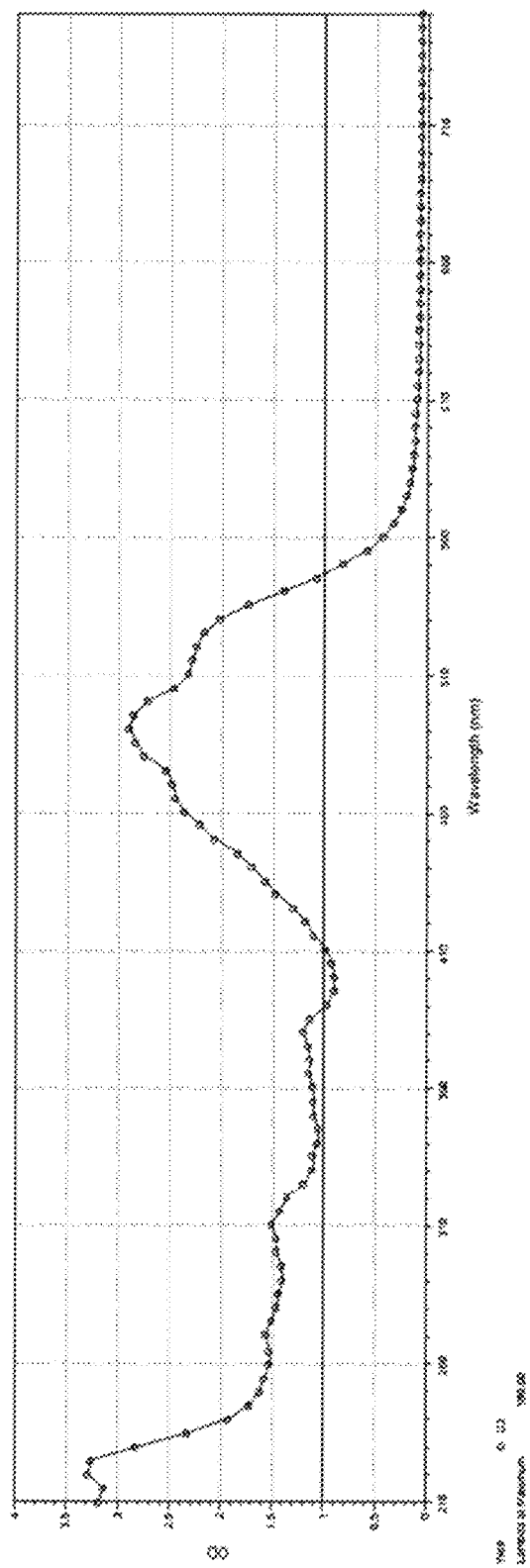
FIG. 3 is an absorption spectrum by full wave scanning of pigment extracted from fermentation product, which is produced by the high concentration methanol tolerant methanotroph *Methylomonas* sp. ZR1 during fermenting to produce carotenoids with methane as substrate in embodiment 4 of the present invention.

Full wave scanning of the red pigment is taken; 300 µl of the pigment solution is taken, and is added into a quartz 96-well plate; while 300 µl of dichloromethane solution is kept as control, the pigment solution is scanned from 220 nm to 700 nm, the scan results are shown in FIG. 3.

The scan results show a three-finger peak which is a typical characteristic peak of carotenoid appears at around 500 nm, which also shows that the red pigment extracted is carotenoids.

Embodiment 5

Fermenting Methanotroph *Methylomonas* sp. ZR1 to Produce Carotenoids by Fermentation with Methane as Substrate Single colony of the methanotroph *Methylomonas* sp. ZR1 formed on the plate is picked, inoculated into 30 ml of NMS liquid culture medium (using methane as carbon source) to culture at 30° C. and at 180 rpm; after being cultured for 2 days, OD$_{600}$ of the NMS liquid culture medium reaches 0.7, and inoculated into fresh NMS culture medium with 5% inoculation, fermenting in column reactor at 28° C., and after being cultured for 5 days, fermentation broth of single colony of methanotroph *Methylomonas* sp.

ZR1 appears to be orange viscous liquid; the methanotroph *Methylomonas* sp. ZR1 is collected by centrifuging for 10 mins at 8000 rpm; the methanotroph *Methylomonas* sp. ZR1 collected is washed twice with distilled water, vacuum freeze-dried, then dried powder of the methanotroph *Methylomonas* sp. ZR1 is obtained; the dried powder of the methanotroph *Methylomonas* sp. ZR1 is weighed, extracted 3 times with methanol solution whose volume is 10 times of dried powder of the methanotroph *Methylomonas* sp. ZR1, then orange extraction solution of pigment is obtained; the orange extraction solution of pigment is filtered, and is dried by the rotary evaporation apparatus, then red pigment is obtained.

The Color Reaction of the Red Pigment in Concentrated Sulfuric Acid

The extracted red pigment is re-dissolved in 1 ml of dichloromethane, then pigment solution is obtained; 50 μl of the pigment solution was taken, diluted with chloroform to 0.5 ml, and being added with a few drops of concentrated sulfuric acid, then the pigment solution turns from red to blue-green, which shows that the red pigment extracted is carotenoids.

Figure 4:
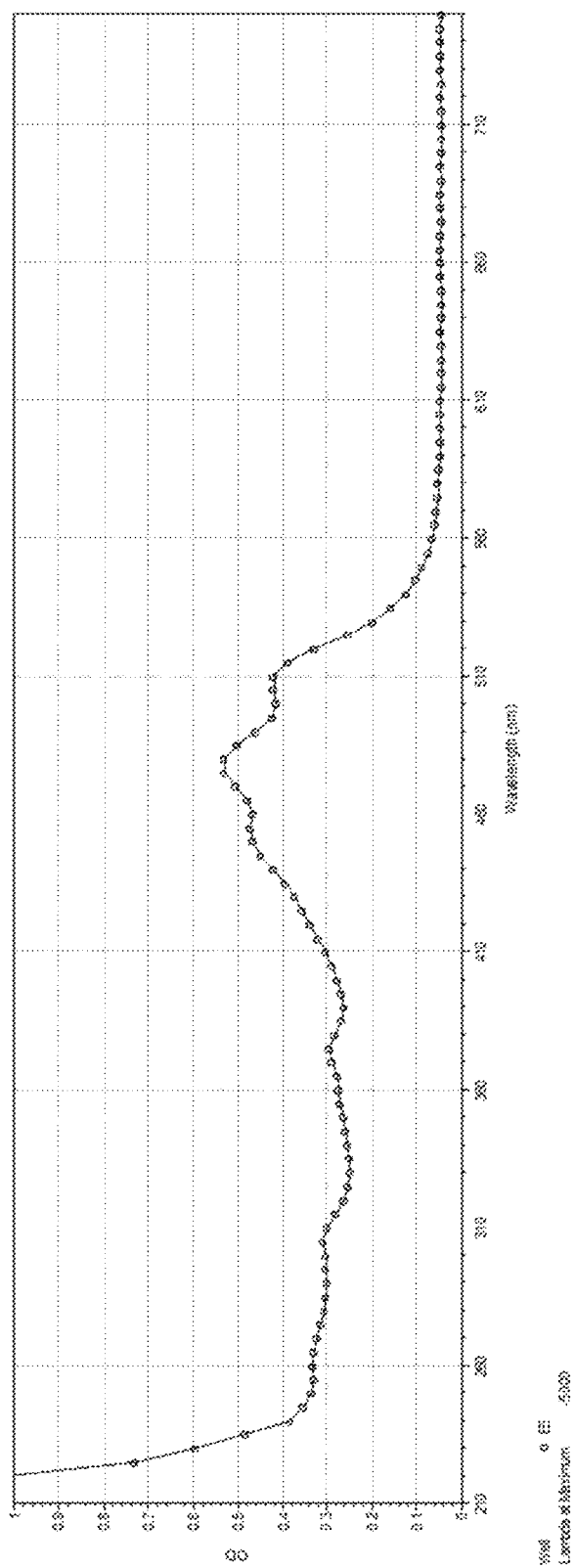
FIG. 4 is an absorption spectrum by full wave scanning of pigment extracted from fermentation product, which is produced by the high concentration methanol tolerant methanotroph *Methylomonas* sp. ZR1 during fermenting to produce carotenoids with methane as substrate in embodiment 5 of the present invention.

Full wave scanning of the red pigment is taken, 300 μl of the pigment solution is taken, and is added into quartz 96-well plate; while 300 μl of dichloromethane solution is kept as control, the pigment solution is scanned from 220 nm to 700 nm, the scan results are shown in FIG. 4, The scan results show a three-finger peak which is a typical characteristic peak of carotenoid appears at around 500 nm, which also shows that the red pigment extracted is carotenoids.

Embodiment 6

Fermenting Methanotroph *Methylomonas* sp. ZR1 to Produce Carotenoids with Methane as Substrate Single colony of the methanotroph *Methylomonas* sp. ZR1 formed on the plate is picked, inoculated into 30 ml of NMS liquid culture medium (using methane as carbon source) to culture at 28° C. and at 180 rpm, after being cultured for 2 days, $OD_{600}$ of the NMS liquid culture medium reaches 0.7, and inoculated into fresh NMS culture medium with 5% inoculation, fermenting in column reactor is conducted at 28° C., and after being cultured for 10 days, fermentation broth of single colony of methanotroph *Methylomonas* sp. ZR1 appears to be orange viscous liquid; the methanotroph is collected by centrifuging for 10 mins at 8000 rpm; the methanotroph collected is washed twice with distilled water, vacuum freeze-dried. then is dried powder of the methanotroph is obtained; dried powder of the methanotroph is weighed, extracted 3 times with methanol solution whose volume is 10 times the volume of dried powder of the methanotroph, then orange extraction solution of pigment is obtained; the orange extraction solution of pigment is filtered, and is dried by the rotary evaporation apparatus, then red pigment is obtained.

The Color Reaction of the Red Pigment in Concentrated Sulfuric Acid

The extracted red pigment is re-dissolved in 1 ml of dichloromethane, then pigment solution is obtained; 50 μl of the pigment solution was taken, diluted with chloroform to 0.5 ml, and being added with a few drops of concentrated sulfuric acid, then the solution turns from red to blue-green, which shows that the red pigment extracted is carotenoids.

Figure 5:
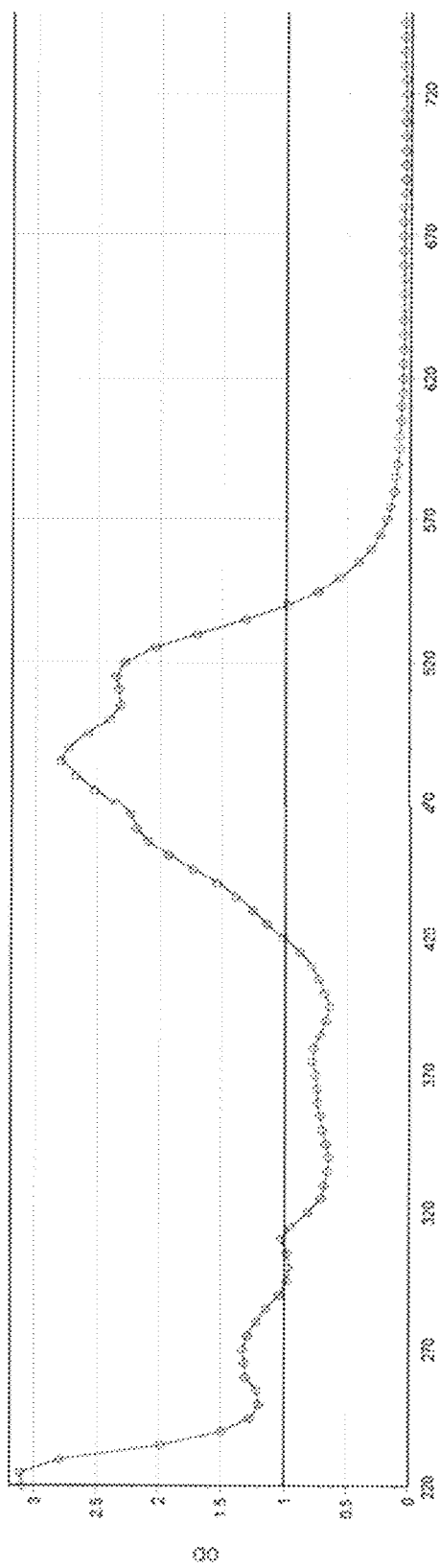
FIG. 5 is an absorption spectrum by full wave scanning of pigment extracted from fermentation product, which is produced by the high concentration methanol tolerant methanotroph *Methylomonas* sp. ZR1 during fermenting to produce carotenoids with methane as substrate in embodiment 6 of the present invention.

Full wave scanning of the red pigment is taken, 300 μl of the pigment solution is taken, and added to a quartz 96-well plate, while 300 μl of dichloromethane solution is kept as control, the pigment solution is scanned from 220 nm to 700 nm, the scan results are shown in FIG. 5.

The scan results show a three-finger peak which is a typical characteristic peak of carotenoid appears at around 500 nm, which also shows that the red pigment extracted is carotenoids.

Embodiment 7

Fermenting Methanotroph *Methylomonas* sp. ZR1 to Produce Polysaccharide with Methane as Substrate Single colony of the methanotroph *Methylomonas* sp. ZR1 formed on the plate is picked, inoculated into 30 ml of NMS liquid culture medium (using methane as carbon source) to culture at 20° C. and at 180 rpm, after being cultured for 2 days, $OD_{600}$ of the NMS liquid culture medium reaches 0.7, and inoculated into fresh NMS culture medium with 5% inoculation, fermenting in column reactor at 20° C., and after being cultured for 3 days, fermentation broth of single colony of methanotroph *Methylomonas* sp. ZR1 appears to be orange viscous liquid; supernatant of the orange viscous liquid is collected by centrifuging for 10 mins at 8000 rpm; volume of the supernatant collected is condensed 10 times through using a rotary evaporator; the supernatant condensed is added with 95% ethanol to make the concentration of ethanol reach 70%, then the supernatant is remained at 4° C. overnight; after being centrifuged for 10 mins at 5000 rpm, supernatant is collected and is washed by ethanol, acetone and petroleum ether in turn, and being dried at 50° C. in an oven, then EPS raw material (polysaccharide) is obtained. The EPS raw material is re-dissolved in distilled water, and then is added into a dialysis bag whose cutoff molecular weight is 3.5 KDa. After being dialyzed for 3 days, and being desalted, polysaccharide solution desalted is obtained. The polysaccharide solution desalted is added with a Sevage solution of the same volume (the volume ratio of chloroform to n-butanol is 4 to 1), and swinging violently for 5 mins, centrifugating for 10 mins at 8000 rpm, collecting the upper polysaccharide solution, then removing protein 6~8 times repeatedly. The deproteinized polysaccharide solution is concentrated under reduced pressure, freeze-dried, then dry polysaccharide samples are obtained.

Qualitative Reaction of Polysaccharide Solution

The Free Polysaccharide Analysis of Polysaccharide Solution 5 mg of dry polysaccharide samples are dissolved in 1 ml of distilled water, then polysaccharide solution is obtained; reducing sugars in the polysaccharide solution are determined by using 3,5-dinitrosalicylic acid, then measurement results show that the polysaccharide solution extracted do not contain free reducing polysaccharides.

MoLish Reaction 5 mg of dry polysaccharide samples are dissolved in 1 ml of distilled water, then polysaccharide solution is obtained; 200 μL of the polysaccharide solution is added into a clean glass test tube, and 100 μl of 6% phenol is added into the clean glass test tube, and 1 ml of concentrated sulfuric acid is added into the clean glass test tube, then color reacting solution of the dry polysaccharide samples is obtained; water is used as a negative control, and glucose is used as a positive control; the solution of the dry polysaccharide samples and the solution of the glucose all show yellow, color of the water do not change.

Figure 6:
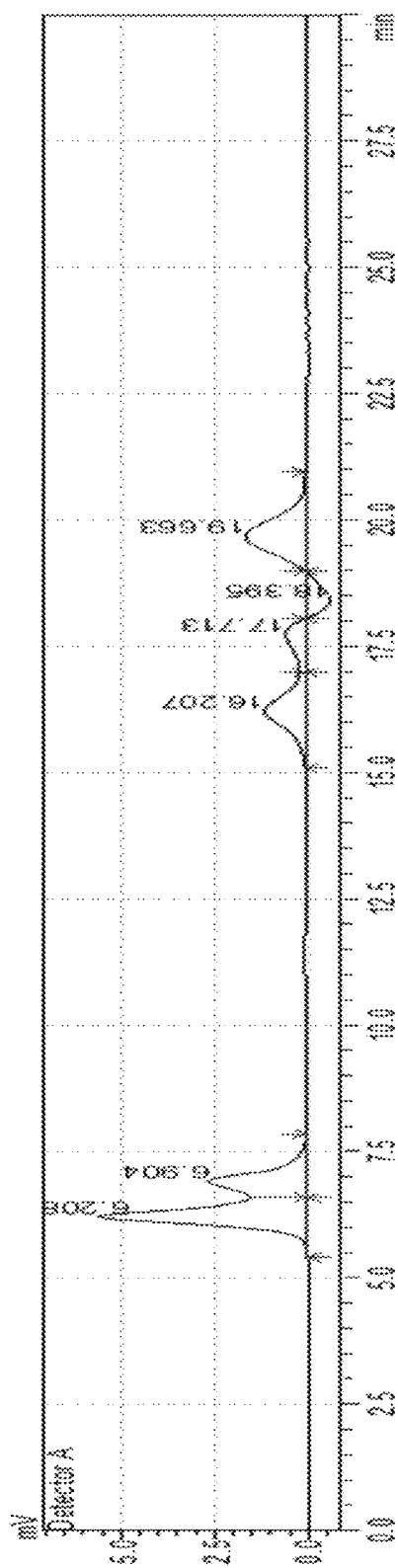
FIG. 6 is a HPLC spectrum of hydrolysate extracted from fermentation product, which is produced by the high concentration methanol tolerant methanotroph *Methylomonas* sp. ZR1 during fermenting to produce polysaccharide with methane as substrate in embodiment 7 of the present invention.

HPLC Analysis of Hydrolysate of Polysaccharide 5 mg of dry polysaccharide samples are dissolved in 1 ml of TFA aqueous solution whose concentration is 4 M; after being hydrolyzed for 8 h at 115° C., hydrolysate of polysaccharide is obtained; HPLC analysis of the hydrolysate of polysaccharide is taken; the HPLC analysis is taken by using BioRad42A column, with ultrapure water as mobile phase, at a flow rate of 0.6 ml/min and at 55° C.; the HPLC analysis is taken by Refractive Index Detector, then HPLC analysis results are shown in FIG. 6.

The HPLC analysis results show that one peak of the hydrolysate of polysaccharide appears at 6.2 min, which is consistent with the time that peak of glucosamine standard sample appears, and another peak of the hydrolysate of polysaccharide appears at 16.2 min, which is consistent with the time that peak of glucose standard sample appears, and another peak of the hydrolysate of polysaccharide appears at 17.8 min, which is consistent with the time that peak of mannose standard sample appears. The HPLC analysis results show the polysaccharides which are produced by the methanotroph *Methylomonas* sp. ZR1 are mainly heteropolysaccharide which is consisted of glucosamine, glucose and mannose.

Embodiment 8

Fermenting Methanotroph *Methylomonas* sp. ZR1 to Produce Polysaccharide with Methane as Substrate Single colony of the methanotroph *Methylomonas* sp. ZR1 formed on the plate is picked, inoculated into 30 ml of NMS liquid culture medium (using methane as carbon source). to culture at 25° C. and at 180 rpm; after being cultured for 2 days, $OD_{600}$ of the NMS liquid culture medium reaches 0.7, and inoculated into fresh NMS culture medium with 5% inoculation; fermenting in column reactor at 28° C., and after being cultured for 6 days, fermentation broth of single colony of methanotroph *Methylomonas* sp. ZR1 appears to be orange viscous liquid; supernatant of the orange viscous liquid is collected by centrifuging for 10 mins at 8000 rpm; volume of the supernatant collected is condensed 10 times through using a rotary evaporator; the supernatant condensed is added with 95% ethanol to make the concentration of ethanol reach 70%, then the supernatant is remained at 4° C. overnight; after being centrifuged for 10 mins at 5000 rpm, supernatant is collected, and is washed by ethanol, acetone and petroleum ether in turn, and being dried at 50° C. in an oven, then EPS raw material (polysaccharide) is obtained. The EPS raw material is re-dissolved in distilled water, and then is added into a dialysis bag whose cutoff molecular weight is 3.5 KDa, and after being dialyzed for 3 days, and being desalted, then polysaccharide solution desalted is obtained. The polysaccharide solution desalted is added with a Sevage solution of the same volume (the volume ratio of chloroform to n-butanol is 4 to 1), and swinging violently for 5 mins, centrifugating for 5 mins at 8000 rpm, collecting the upper polysaccharide solution, then removing protein 6~8 times repeatedly. The polysaccharide solution removed protein is concentrated under reduced pressure, freeze-dried, then dry polysaccharide samples are obtained.

Qualitative Reaction of Polysaccharide Solution

The Free Polysaccharide Analysis of Polysaccharide Solution 5 mg of dry polysaccharide samples are dissolved in 1 ml of distilled water, then polysaccharide solution is obtained; reducing sugars in the polysaccharide solution are determined by using 3,5-dinitrosalicylic acid, then the measurement results show that the polysaccharide solution extracted do not contain free reducing polysaccharides.

MoLish Reaction 5 mg of dry polysaccharide samples is dissolved in 1 ml of distilled water, then polysaccharide solution is obtained; 200 μL of the polysaccharide solution is added into a clean glass test tube, then 100 μl of 6% phenol is added into the clean glass test tube, and 1 ml of concentrated sulfuric acid is added into the clean glass test tube, then color reacting solution of the dry polysaccharide samples is obtained; water is used as a negative control, and glucose is used as a positive control; the solution of the dry polysaccharide samples and the solution of the glucose all show yellow, color of the water do not change.

Figure 7:
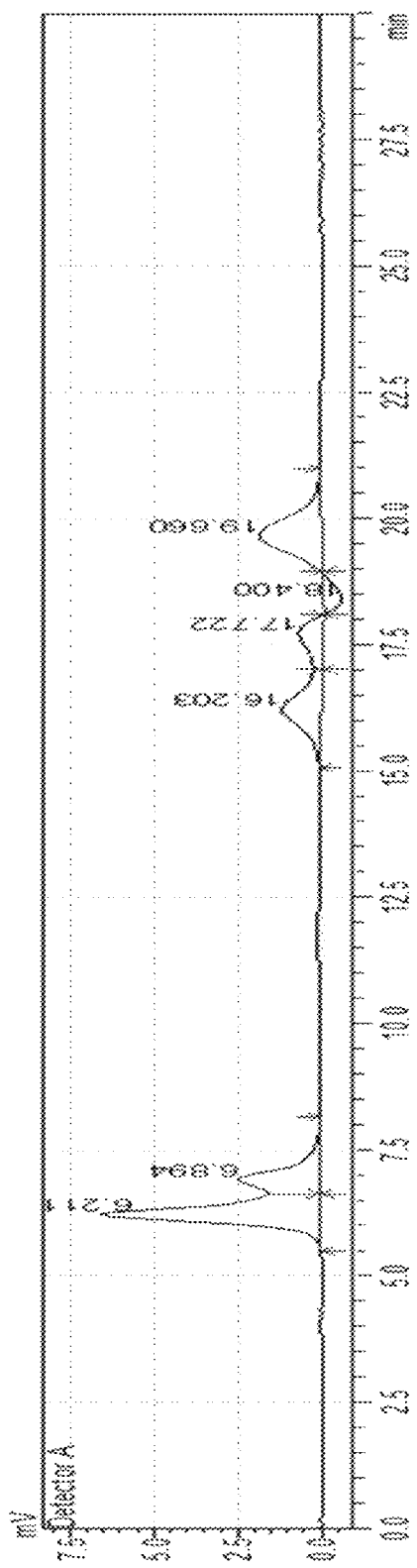
FIG. 7 is a HPLC spectrum of hydrolysate extracted from fermentation product, which is produced by the high concentration methanol tolerant methanotroph *Methylomonas* sp. ZR1 during fermenting to produce polysaccharide with methane as substrate in embodiment 8 of the present invention.

HPLC Analysis of Hydrolysate of Polysaccharide 5 mg of dry polysaccharide samples are dissolved in 1 ml of TFA aqueous solution whose concentration is 4 M; after being hydrolyzed for 8 h at 115° C., hydrolysate of polysaccharide is obtained; HPLC analysis of the hydrolysate of polysaccharide is taken; the HPLC analysis is taken by using BioRad42A column, with ultrapure water as mobile phase, at a flow rate of 0.6 ml/min and at 55° C.; the HPLC analysis is taken by Refractive Index Detector then HPLC analysis results are shown in FIG. 7.

The HPLC analysis results show one peak of the hydrolysate of polysaccharide appears at 6.2 min, which is consistent with the time that peak of glucosamine standard sample appears, and another peak of the hydrolysate of polysaccharide appears at 16.2 min, which is consistent with the time that peak of glucose standard sample appears, and another peak of the hydrolysate of polysaccharide appears at 17.8 min, which is consistent with the time that peak of mannose standard sample appears. The HPLC analysis results show the polysaccharides which are produced by the methanotroph *Methylomonas* sp. ZR1 are mainly heteropolysaccharide, which includes glucosamine glucose and mannose.

Embodiment 9

Fermenting Methanotroph *Methylomonas* sp. ZR1 to Produce Polysaccharide with Methane as Substrate Single colony of the methanotroph *Methylomonas* sp. ZR1 formed on the plate is picked, inoculated into 30 ml of NMS liquid culture medium (using methane as carbon source) to culture at 28° C. and at 180 rpm, after being cultured for 2 days, $OD_{600}$ of the NMS liquid culture medium reached 0.7, and inoculated into fresh NMS culture medium with 5% inoculation, fermenting in column reactor at 28° C., and after being cultured for 10 days, fermentation broth of single colony of methanotroph *Methylomonas* sp. ZR1 appears to be orange viscous liquid; supernatant of the orange viscous liquid is collected by centrifuging for 10 mins at 8000 rpm; volume of the supernatant collected is condensed 10 times through using a rotary evaporator; the supernatant condensed is added with 95% ethanol to make the concentration of ethanol reach 70%, then the supernatant is remained at 4° C. overnight; after being centrifuged for about 10 mins at 5000 rpm, supernatant is collected, and is washed by ethanol, acetone and petroleum ether in turn, and being dried at 50° C. in an oven, then EPS raw material (polysaccharide) is obtained. The EPS raw material is re-dissolved in distilled water, and then is added into a dialysis bag whose cutoff molecular weight is 3.5 KDa. After being dialyzed for 3 days, and being desalted, then polysaccharide solution desalted is obtained. The polysaccharide solution desalted is added with a Sevage solution of the same volume (the volume ratio of chloroform to n-butanol is 4 to 1), and swinging violently for 5 mins, centrifugating for 10 mins at 8000 rpm, collecting the upper polysaccharide solution, then removing protein 6~8 times repeatedly. The deproteinized polysaccharide solution is concentrated under reduced pressure, freeze-dried, then dry polysaccharide samples are obtained.

Qualitative Reaction of Polysaccharide Solution

The Free Polysaccharide Analysis of Polysaccharide Solution 5 mg of dry polysaccharide samples are dissolved in 1 ml of distilled water, then polysaccharide solution is obtained; reducing sugars in the polysaccharide solution are determined by using 3,5-dinitrosalicylic acid, then measurement results show that the polysaccharide solution extracted does not contain free of reducing polysaccharides.

MoLish Reaction 5 mg of dry polysaccharide samples is dissolved in 1 ml of distilled water, then polysaccharide solution is obtained; 200 μL of the polysaccharide solution is added to a clean glass test tube, and 100 μl of 6% phenol is added into the clean glass test tube, and 1 ml of concentrated sulfuric acid is added into the clean glass test tube, then color reacting solution of the dry polysaccharide samples is obtained; water is used as a negative control, and glucose is used as a positive control; the solution of the dry polysaccharide samples and the solution of the glucose all show yellow, color of the water do not change.

Figure 8:
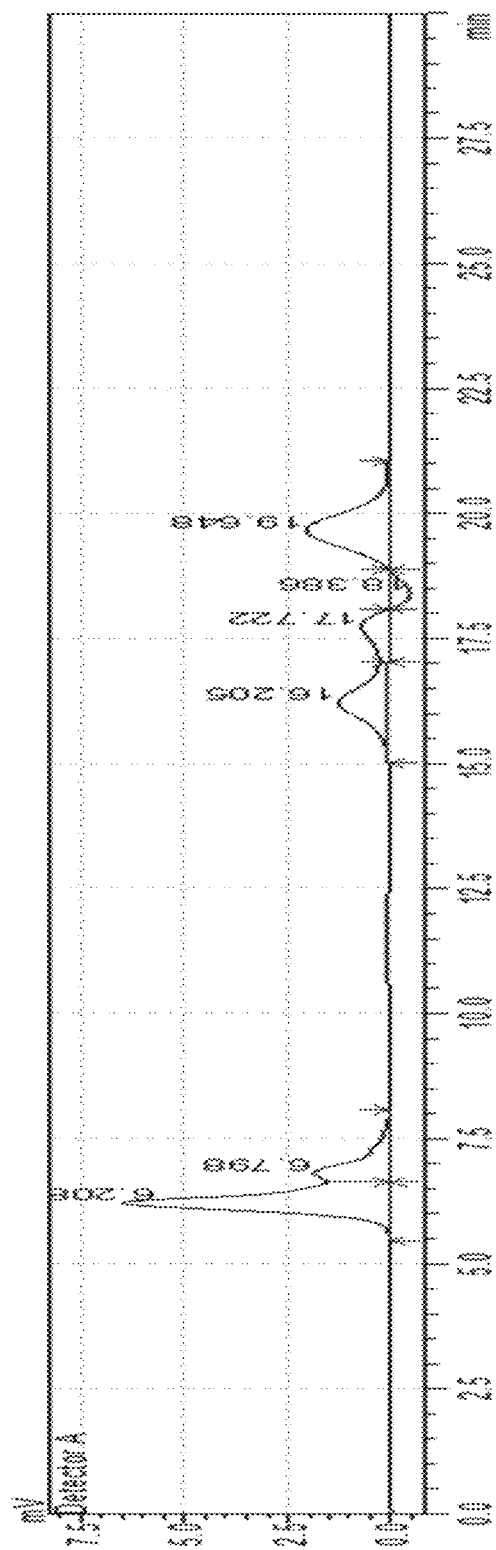
FIG. 8 is a HPLC spectrum of hydrolysate extracted from fermentation product, which is produced by the high concentration methanol tolerant methanotroph *Methylomonas* sp. ZR1 during fermenting to produce polysaccharide with methane as substrate in embodiment 9 of the present invention.

HPLC Analysis of Hydrolysate of Polysaccharide 5 mg of dry polysaccharide samples dissolved in 1 ml of TFA aqueous solution whose concentration is 4 M, after being hydrolyzed for 8 h at 115° C., hydrolysate of polysaccharide is obtained; HPLC analysis of the hydrolysate of polysaccharide is taken. the HPLC analysis is taken by using BioRad42A column, with ultrapure water as mobile phase, at a flow rate of 0.6 ml/min, at 55° C.; the HPLC analysis is taken by Refractive Index Detector, then HPLC analysis results are shown in FIG. 8.

The HPLC analysis results show that one peak of the hydrolysate of polysaccharide appears at 6.2 min, which is consistent with the time that peak of glucosamine standard sample appears, and another peak of the hydrolysate of polysaccharide appears at 16.2 min, which is consistent with the time peak of glucose standard sample appears, and another peak of the hydrolysate of polysaccharide appears at 17.8 min, which is consistent with the time peak of mannose standard sample appears. The HPLC analysis results show the polysaccharides which are produced by the methanotroph *Methylomonas* sp. ZR1 are mainly heteropolysaccharide, which includes glucosamine, glucose and mannose.

Although the embodiments of the present invention have been disclosed above, but it is not limited to the use of the specification and embodiments listed. It can be applied to various fields suitable for the present invention. Those skilled in the art can easily modify. Therefore, without departing from the general concept of the scope defined by the claims and the equivalents, the present invention is not limited to the specific details and illustrations herein illustrated and described herein.

What is claimed is:

1. A method for producing carotenoids, comprising
   (a) culturing a high-concentration-methanol-tolerant methanotroph named *Methylomonas* strain ZR1, having the accession number of CGMCC No. 9873 in the China General Microbiological Culture Collection Center in fermentation in a medium comprising at least 1% methanol or in a vessel comprising a gaseous mixture that is at least 15% methane, and
   (b) harvesting the carotenoids made in step (a).

2. The method of claim 1, wherein the fermentation is carried out at a temperature of 20-30° C.

3. The method of claim 2, wherein the fermentation temperature is 25° C.

4. The method of claim 3, wherein when the methanol is used as the substrate, the mass percent concentration of the methanol in the fermentation culture medium is less than or equal to 3.5%.

* * * * *